United States Patent
Cheng et al.

(10) Patent No.: US 8,801,692 B2
(45) Date of Patent: Aug. 12, 2014

(54) GRADIENT COATED STENT AND METHOD OF FABRICATION

(75) Inventors: Peiwen Cheng, Santa Rosa, CA (US); Patrice Tremble, Santa Rosa, CA (US); Wenda Carlyle, Silverado, CA (US); Diane Judd, Minneapolis, MN (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1211 days.

(21) Appl. No.: 10/921,735

(22) Filed: Aug. 18, 2004

(65) Prior Publication Data

US 2005/0075714 A1    Apr. 7, 2005

Related U.S. Application Data

(60) Provisional application No. 60/505,675, filed on Sep. 24, 2003.

(51) Int. Cl.
*A61M 31/00* (2006.01)
*A61F 2/06* (2013.01)
*A61L 33/00* (2006.01)

(52) U.S. Cl.
USPC .......................... 604/509; 623/1.11; 427/2.24

(58) Field of Classification Search
USPC ................... 623/11.11, 1.11, 1.15, 1.4–1.46; 604/509; 427/2.24; 606/192–198
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau | |
| 5,609,629 A * | 3/1997 | Fearnot et al. | 623/1.42 |
| 5,634,946 A * | 6/1997 | Slepian | 128/898 |
| 5,648,442 A | 7/1997 | Bowers et al. | |
| 5,776,184 A | 7/1998 | Tuch et al. | |
| 5,824,048 A * | 10/1998 | Tuch | 128/898 |
| 6,090,127 A | 7/2000 | Globerman | |
| 6,329,386 B1 | 12/2001 | Mollison | |
| 6,358,556 B1 * | 3/2002 | Ding et al. | 427/2.24 |
| 6,368,658 B1 * | 4/2002 | Schwarz et al. | 427/2.15 |
| 6,638,301 B1 * | 10/2003 | Chandrasekaran et al. | 623/1.34 |
| 7,169,178 B1 * | 1/2007 | Santos et al. | 623/1.42 |
| 7,491,233 B1 * | 2/2009 | Ding et al. | 623/1.42 |
| 2001/0022988 A1 * | 9/2001 | Schwarz et al. | 427/2.1 |

(Continued)

FOREIGN PATENT DOCUMENTS

EP    0623354    11/1994
WO   WO 2004/026361    4/2004

*Primary Examiner* — Darwin Erezo
*Assistant Examiner* — Richard Louis

(57) ABSTRACT

The gradient coated stent 150 of the present invention provides a coated stent having a continuous coating 130 disposed on the stent elements. The continuous coating 130 includes a first coating component and a second coating component. The concentration of the first coating component varies continuously over at least part of the thickness of the continuous coating 130. The concentration of the second coating component can also vary over at least part of the thickness of the continuous coating 130. In one embodiment, the concentration of the first coating component decreases in the direction from the stent element towards the outer edge of the continuous coating 130 and the concentration of the second coating component increases in the direction from the stent element towards the outer edge of the continuous coating 130.

36 Claims, 11 Drawing Sheets

(56) References Cited

U.S. PATENT DOCUMENTS

| | | | |
|---|---|---|---|
| 2002/0016574 A1* | 2/2002 | Wang et al. | 604/264 |
| 2002/0122877 A1* | 9/2002 | Harish et al. | 427/2.24 |
| 2002/0127327 A1 | 9/2002 | Schwarz et al. | |
| 2003/0003221 A1 | 1/2003 | Zhong et al. | |
| 2003/0068355 A1* | 4/2003 | Shanley et al. | 424/426 |
| 2003/0143315 A1* | 7/2003 | Pui et al. | 427/2.1 |
| 2003/0175410 A1* | 9/2003 | Campbell et al. | 427/2.24 |
| 2004/0028655 A1* | 2/2004 | Nelson et al. | 424/93.2 |

* cited by examiner

GRADIENT COATED STENT AND METHOD OF FABRICATION

RELATED APPLICATIONS

This application claims the benefit of U.S. Provisional Patent Application 60/505,675 filed Sep. 24, 2003.

TECHNICAL FIELD

The technical field of this disclosure is medical implant devices, particularly, a gradient coated stent and methods of making the same.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

Stents have been used with coatings to deliver drug or other therapy to the patient at the site of the stent, such as the interior wall of an artery or vessel. Typically, the coating forms a uniform radial layer over the stent elements with a fixed ratio of drug to polymer. Although many factors (such as the hydrophilicity, hydrophobicity, and molecular size of the drug, and the hydrophilicity, hydrophobicity, amorphous, crystallinity, morphology, glass transition temperature of the polymer matrix) affect the diffusion rate of the drug from the coating, the diffusion rate is generally proportional to the difference in drug concentration across the coating ($\Delta C$). This causes problems with the dose of drug delivered with time. Initially, the drug concentration is high, so a large quantity of drug is released. This is called burst releasing and results in local tissue damage for certain drugs that are toxic in high doses. Later after implantation, the drug concentration is depleted and the $\Delta C$ become smaller and smaller, so little drug is released. This results in delivery of a less-than-effective dose. With a uniform radial drug coating, stent designer must choose between a stent which risks initial tissue damage and a stent which has a limited effective drug lifetime.

A uniform drug coating may not provide the most effective therapy over time. Immediately after stent implantation, inflammation and thrombosis occur due to the tissue trauma from the angioplasty and the presence of the stent. While the inflammation normally subsides after a few days, tissue growth may result in restenosis three to six months after stent implantation. A uniform, single drug coating is unable to treat both conditions. Anti-inflammatory drugs are desirable initially, but anti-proliferative drugs are required later.

There are also difficulties associated with manufacturing stents having multiple components or multiple layers. The coating is typically applied to the stent by dipping or spraying the stent with a liquid containing the drug or therapeutic agent dispersed in a polymer/solvent mixture. The liquid coating then dries to a solid uniform coating. Combinations of dipping and spraying can also be used.

Problems also arise during manufacture when the drugs, polymers, or solvents are incompatible. For example, one solvent may be suitable for a particular drug, but unsuitable for a particular polymer. The combination of a particular drug and a particular polymer may be incompatible and one or the other degrade when held in solution too long. Incompatibility results in ineffective drugs or defective coatings.

Manufacturing techniques producing multiple coating layers with varying characteristics have been developed, but such methods increase the time and expense of manufacturing. Separate steps are required to apply each coating layer, which must dry and have its surface prepared before the next layer is applied. In dip coating, several pots holding solutions with different drug/polymer ratios can be prepared. The stent is then dipped in each pot, starting with the solution of highest drug/polymer ratio and ending with the lowest to form a profile coating. In such a stepwise approach, however, each drug/polymer coat can be dissolved by subsequent dip process if similar solvent is used. Poor surface preparation and layer incompatibilities can cause voids and defects at the boundaries between coating layers.

It would be desirable to have a gradient coated stent and methods of making the same that would overcome the above disadvantages.

SUMMARY OF THE INVENTION

One aspect of the present invention provides a stent with a gradient coating in which at least one coating component varies continuously with coating thickness.

Another aspect of the present invention provides a stent with a gradient coating to avoid burst release and to deliver an appropriate long-term drug release.

Another aspect of the present invention provides a stent with a gradient coating with a high concentration of a therapeutic agent at the inner edge of the stent coating and a low concentration at the outer edge of the stent coating.

Another aspect of the present invention provides a stent with a gradient coating having a linear drug gradient or step-gradient to generate desired elution profiles.

Another aspect of the present invention provides a stent with a gradient coating able to deliver different drug therapies as a function of time.

Another aspect of the present invention provides a method of manufacture for a gradient coated stent with coatings formed from generally incompatible materials.

Another aspect of the present invention provides a method of manufacture for a gradient coated stent avoiding dissolving subsequent layers.

Another aspect of the present invention provides a method of manufacture for a gradient coated stent generating a cap coat in a single step after spraying a drug/polymer solution.

Another aspect of the present invention provides a method of manufacture for a gradient coated stent providing a uninterrupted process of stent coating.

Another aspect of the present invention provides a method of manufacture for a gradient coated stent reducing labor and allowing process automation.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENT

Figure 1:
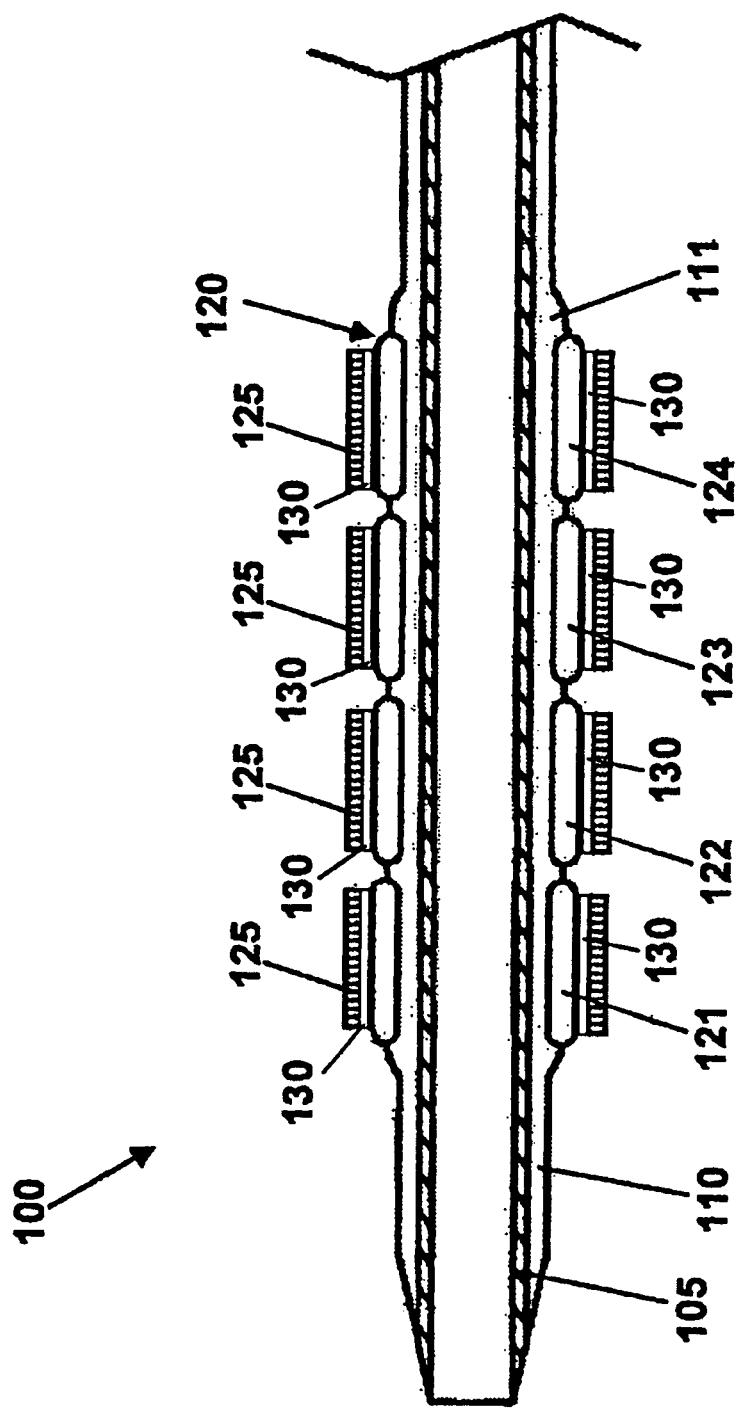
FIG. 1 shows a stent delivery system made in accordance with the present invention.

FIG. 1 shows a stent delivery system made in accordance with the present invention. The stent delivery system 100 includes a catheter 105, a balloon 110 operably attached to the catheter 105, and a stent 120 disposed on the balloon 110. The balloon 110, shown in a collapsed state, may be any variety of balloons capable of expanding the stent 120. The balloon 110 may be manufactured from a material such as polyethylene, polyethylene terephthalate (PET), nylon, Pebax® polyetherblock co-polyamide polymers, or the like. In one embodiment, the balloon 110 may include retention means 111, such as mechanical or adhesive structures, for retaining the stent 120 on the balloon 110 until it is deployed. The catheter 105 may be any variety of balloon catheters, such as a PTCA (percutaneous transluminal coronary angioplasty) balloon catheter, capable of supporting a balloon during angioplasty.

The stent 120 may be any variety of implantable prosthetic devices known in the art and capable of carrying a coating. In one embodiment, the stent 120 may have a plurality of identical cylindrical stent segments placed end to end. Four stent segments 121, 122, 123, and 124 are shown, and it will be recognized by those skilled in the art that an alternate number of stent segments may be used.

The stent 120 includes at least one continuous coating 130. The continuous coating 130 is typically a polymer coating carrying one or more therapeutic agents, such as anti-inflammatory agents or anti-proliferative agents. The continuous coating 130 is merely exemplary: other coating configurations, such as multiple coating layers on top of the continuous coating 130, are possible. Although the continuous coating 130 are shown schematically on the outer circumference of the stent 120, the continuous coating 130 can coat the whole stent 120, both inside and outside, and around the cross section of individual stent elements. The continuous coating 130 can be any coating that can elute a therapeutic agent and maintain coverage of the stent elements. The coating components, such as the therapeutic agent or the polymer, vary continuously over the thickness of the continuous coating 130.

Figure 2:
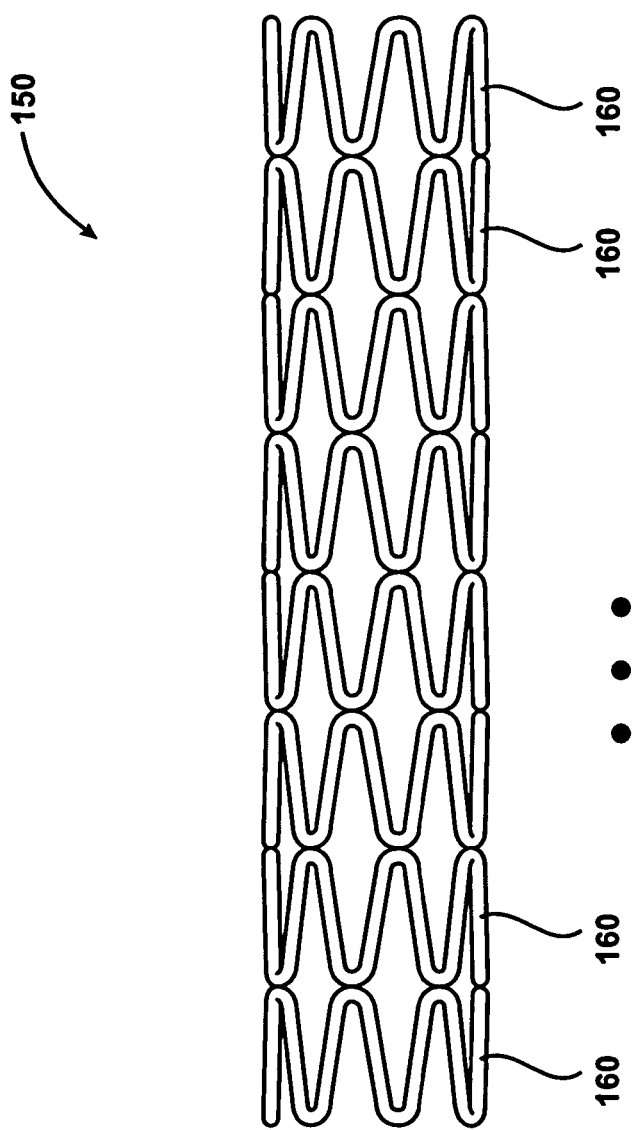
FIGS. 2 & 3 show a stent and a cross section, respectively, of a coated stent made in accordance with the present invention.

FIG. 2 shows a coated stent made in accordance with the present invention. The stent 150 comprises a number of segments 160. The pattern of the segments 160 can be W-shaped or can be a more complex shape with the elements of one segment continuing into the adjacent segment. The stent 150 can be installed in the stent delivery system of FIG. 1 for implantation in a body lumen.

Referring to FIG. 2, the stent 150 is conventional to stents generally and can be made of a wide variety of medical implantable materials, such as stainless steel (particularly 316-L or 316LS stainless steel), MP35 alloy, nitinol, tantalum, ceramic, nickel, titanium, aluminum, polymeric materials, tantalum, MP35N, titanium ASTM F63-83 Grade 1, niobium, high carat gold K 19-22, and combinations thereof. The stent 150 can be formed through various methods as well. The stent 150 can be welded, laser cut, molded, or consist of filaments or fibers which are wound or braided together in order to form a continuous structure. Depending on the material, the stent can be self-expanding, or be expanded by a balloon or some other device. The continuous coating can be disposed on the surface of the segments 160.

Figure 3:
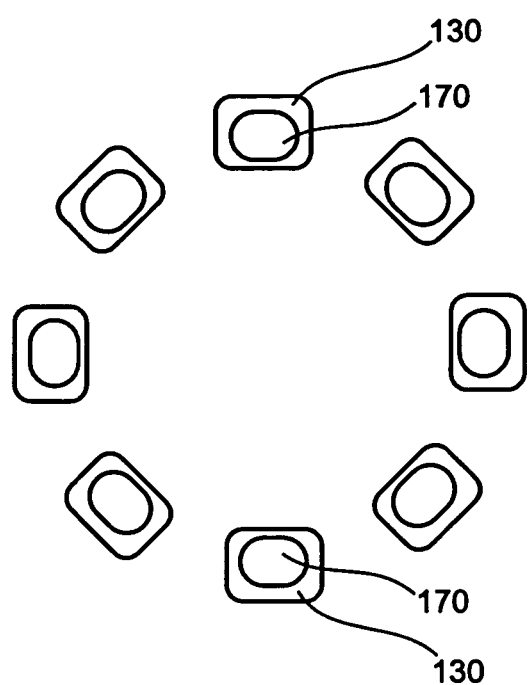

FIG. 3 shows a cross section of a coated stent made in accordance with the present invention. A plurality of stent elements 170 are provided with a continuous coating 130. The stent elements form the segments which form the stent. Although the cross section of the stent elements 170 is shown as generally rectangular with rounded corners, the cross section can be any number of shapes depending on fabrication methods, materials, and desired effect. The cross section of the stent elements 170 can be circular, ellipsoidal, rectangular, hexagonal, square, polygonal, or of other cross-sectional shapes as desired.

The continuous coating 130 comprises coating components, such as polymers and therapeutic agents. One or more polymers typically form the bulk of the continuous coating 130. The therapeutic agents, such as anti-inflammatory or anti-proliferative agents, are dispersed in the polymer. The therapeutic agent can be dissolved throughout the polymer, or can be dispersed throughout the polymer in discrete units like nano-particles. One or more therapeutic agents can be used to accomplish the desired result.

Nano-particles can be used when a common solvent for drug and polymer cannot be found or when further control of the therapeutic agent is needed. In one embodiment, nano-particles are small particles of crystalline therapeutic agents ground to a small size, such as nanometer-sized particles. Such nano-particles increase the speed of delivery of the anti-proliferative agent because of the large surface area to volume ratio. In another embodiment, the nano-particles can include a therapeutic agent as a core and a polymer as a shell. The polymer acts as barrier to further control the release profile. Nano-particles can be formed by many methods suitable for the particular therapeutic agent and known to those in the art, including oil in water, water in oil, oil in water in oil.

The concentration of the therapeutic agent in the polymer varies continuously over the thickness of the continuous coating 130. Different profiles of the therapeutic agent can accomplish different therapeutic results. For example, a high concentration of therapeutic agent in the continuous coating 130 near the stent element 170 with a low concentration in the continuous coating 130 at the outer edge will suppress any burst release and provide a steady long-term dose. Additional coating layers can be applied on top of the continuous coating 130 to provide particular release effects or to act as a cap coat to establish desirable mechanical properties for the exposed surface of the stent.

In one embodiment, the continuous coating 130 can be made of a biodegradable or erodible material. Biodegradable polymer coatings release the therapeutic agent with degradation of the polymer. The products of degradation are weak organic acids, water, and carbon dioxide. Erodible materials include natural polymers, such as a carbohydrate or gelatin, or a synthetic polymer, such as polyglycolide. Erodible materials that can be used for the continuous coating 130, include, but are not limited to, poly(D-lactic acid), poly(L-lactic acid), poly(☐caprolactone), and copolymers or terpolymers of any two or all three of these monomers; polyhydroxyalkanoates, such as poly(hydroxybutyrate), poly(hydroxyvalerate), or copolymers thereof (e.g. poly(hydroxybutyrate-co-valerate)); polydioxanone; polyorthoester; polyanhydride; poly(propylene fumarate); poly(glycolic acid-co-trimethylene carbonate); polyphosphoester; polyphosphoester urethane; poly(amino acids); poly(alkyl cyanoacrylates); poly(trimethylene carbonate); poly(iminocarbonate); copoly(ether-esters) (e.g. PEO/PLA); poly(ester amides); poly(ester-urethane); polyalkylene oxalates; polyphosphazenes; copolymers, terpolymers, blends, and copolymer blends of the above; combinations of the above; and the like.

Biomacromolecules and their variants that can be used for the continuous coating 130, include, but are not limited to, fibrin; fibrinogen; cellulose; starch; collagen and hyaluronic acid; hydrogels; polyhydroxyacids; polysaccharides; polyamines; polyaminoacids; polyamides; polycarbonates; silk; keratin; collagen; gelatin; fibrinogen; elastin; actin; myosin; cellulose; amylose; dextran; chitin; glycosaminoglycans; proteins; protein based polymers (e.g. polypeptides); copolymers, terpolymers, blends, and copolymer blends of the above; combinations of the above; and the like.

In one embodiment, the continuous coating 130 can be made of a non-biodegradable material, such as phosphorylcholine polymer from Biocompatibles International plc as set forth in U.S. Pat. No. 5,648,442. Non-biodegradable polymers can be divided into two classes. The first class is hydrophobic polymers and the second class is hydrophilic polymers. Hydrophobic polymers that can be used for the continuous coating 130, include, but are not limited to, polyolefins; acrylate polymers; vinyl polymers; styrene polymers; polyurethanes; polyesters; epoxy; polysiloxane; natural polymers; variants, copolymers, terpolymers, blends, and copolymer blends of the above; combinations of the above; and the like. Hydrophilic polymers or hydrogels that can be used for the continuous coating 130, include, but are not limited to, polyacrylic acid; polyvinyl alcohol; poly(N-vinylpyrrolidone); poly(hydroxyl, alkymethacrylate); polyethylene oxide; hyaluronon; variants, copolymers, terpolymers, blends, and copolymer blends of the above; combinations of the above; and the like.

In one embodiment, the therapeutic agent in the continuous coating 130 can be an anti-inflammatory agent, such as a steroid. Anti-inflammatory agents that can be used in the continuous coating 130, include, but are not limited to, steroidal anti-inflammatory agents, non-steroidal anti-inflammatory agents, hydrocortisone, hydrocortisone acetate, dexamethasone, dexamethasone 21-phosphate, fluocinolone, medrysone, prednisolone acetate, fluoromethalone, betamethasone, triaminolone, ibuprofen, ketoprofen, piroxicam, naproxen, sulindac, choline subsalicylate, diflunisal, fenoprofen, indomethacin, meclofenamate, salsalate, tolmetin, magnesium salicylate, diclofenac, enoxaprin, angiopeptin, monoclonal antibodies, hirudin, acetylsalicylic acid, amlodipine, doxazosin and combinations thereof. Additional anti-inflammatory agents to achieve a desired result, such as those included in the *Merck Index: An Encyclopedia of Chemicals, Drugs, & Biologicals* published by the Merck Publishing Group and incorporated herein by reference, are well known to those skilled in the art.

In one embodiment, the therapeutic agent in the continuous coating 130 can be an anti-proliferative agent, such as the drug 42-Epi-(tetrazolyl)-rapamycin, set forth in U.S. Pat. No. 6,329,386 assigned to Abbott Laboratories, Abbott Park, Ill. Other anti-proliferative agents that can be used in the continuous coating 130, include, but are not limited to, rapamycin and rapamycin anglogs such as ABT-578 tetrazole-containing macrocyclic immunosuppressant from Abbott Laboratories; statins; actinomycin; paclitaxel; 5-fluorouracil; cisplatin; vinblastine; vincristine; epothilones; methotrexate; azathioprine; adriamycin; mutamycin; endostatin; angiostatin; thymidine kinase inhibitors; and combinations thereof. Additional anti-neoplastic agents to achieve a desired result, such as those included in the *Merck Index: An Encyclopedia of Chemicals, Drugs, & Biologicals* published by the Merck Publishing Group and incorporated herein by reference, are well known to those skilled in the art.

Those skilled in the art will appreciate that a number of therapeutic agents can be used in the continuous coating 130 to beneficial effect. Protein and gene therapy agents can be included. Therapeutic agents may limit or prevent the restenosis. For example, antithrombogenic agents such as heparin or clotting cascade IIb/IIIa inhibitors (e.g., abciximab and eptifibatide) can be included to diminish thrombus formation. Such agents may effectively limit clot formation at or near the implanted device. Additional therapeutic agents can be used in the continuous coating 130 include antinflammatory agents; antioxidants; immunosuppressants; antisense agents; antiangiogenesis agents; antiendothelin agents; antimitogenic factors; antiplatelet agents; antiproliferative agents; antithrombogenic agents; antibiotics; antiinfective agents; antidiabetic agents; antiarteriosclerotics; antiarythmics; calcium channel blockers; clot dissolving enzymes; growth factors; growth factor inhibitors; nitrates; nitric oxide releasing agents; vasodilators; virus-mediated gene transfer agents; agents having a desirable therapeutic application; combinations of the above; and the like. A variety of other drugs may also be included to modulate localized immune response, limit hyperplasia, or provide other benefits.

Figure 4A:
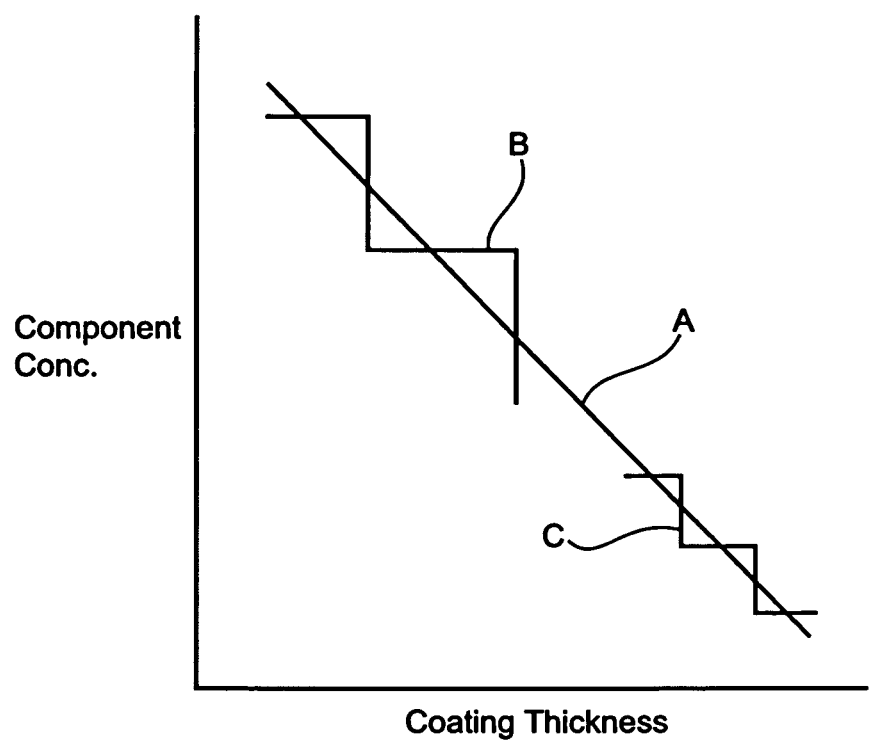
FIGS. 4A-4C show exemplary graphs of coating component concentration versus coating thickness for a coated stent made in accordance with the present invention.
Figure 4B:
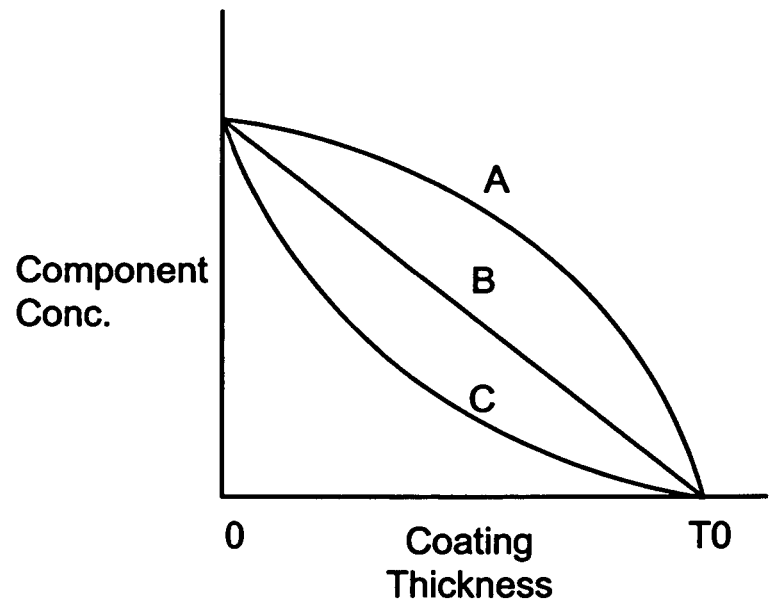
Figure 4C:
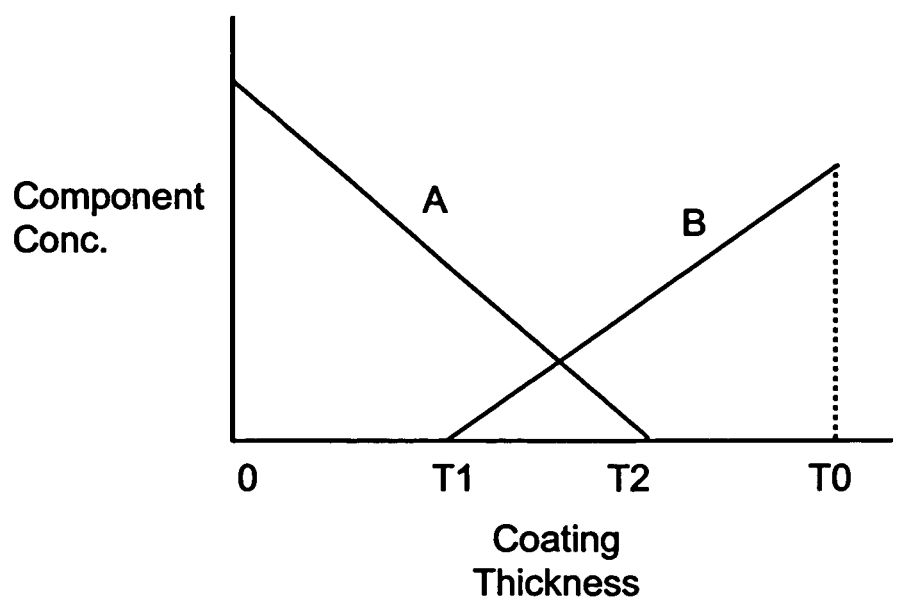

FIGS. 4A-4C show exemplary graphs of coating component concentration versus coating thickness for a coated stent made in accordance with the present invention. The coating component can be any component for which it is desired to vary the concentration with coating thickness, including, but not limited to, drugs, therapeutic agents, and polymers.

FIG. 4A shows a graph of coating component concentration versus coating thickness for coated stents formed by discrete steps and continuous coating. Profile A shows a linear gradient coating having decreasing coating component concentration with increasing thickness. Profile B shows coating concentration formed in a series of large steps, such as formed by dip coating a stent in a series of solutions where each solution has a smaller coating component concentration. Profile C shows coating concentration formed in a series of small steps, such as formed by dip coating a stent in a series of solutions where each solution has a smaller coating component concentration and a greater number of dip coating steps are performed. Profile C more closely approaches the linear gradient of Profile A than does Profile B. As the number of dip coating steps becomes large and the change in coating component concentration between steps becomes small, the step coating result will approach the linear gradient of Profile A.

FIG. 4B shows a graph of coating component concentration versus coating thickness for a coated stent having decreasing coating component concentration with increasing thickness. In these three embodiments, the coating component concentration is a maximum at the zero coating thickness at the stent element and declines to a minimum at the coating thickness TO at the exterior of the stent. Profile B is has a linear gradient, while profile A is concave down and profile C is concave up. The three profiles illustrate how a continuously varying coating component can be tailored for a desired result.

If the coating component is a drug or other therapeutic agent, these profiles avoid burst release and provide effective long-term drug dosage. The drug near the exterior, which is delivered shortly after implantation, is limited. The major portion of the drug is located toward the stent element, where it can be delivered long-term as the exterior drug depletes. The gradients and the endpoints of the profiles can be tailored for particular drug release characteristics.

If the coating component is a constituent polymer, the coating near the exterior can be designed to erode quickly and the coating toward the stent element designed to erode slowly or not at all. For a coating including a durable polymer and an erodible polymer, providing a lower concentration of the durable polymer near the exterior allows the exterior to erode rapidly. Providing a higher concentration of the durable polymer toward the stent element keeps the stent element covered and maintains a long-term drug reservoir. The gradients and the endpoints of the profiles can be tailored for particular coating behaviors.

FIG. 4C shows a graph of coating component concentration versus coating thickness for a coated stent having at least two coating components of varying concentration. Profile A shows the concentration of a first coating component and profile B shows the concentration of a second coating component. The first and second coating components can be any components for which it is desired to vary the concentration with coating thickness, including, but not limited to, drugs, therapeutic agents, and polymers.

The first coating component concentration of profile A is highest at the zero coating thickness at the stent element and declines to a minimum at the coating thickness T2 within the stent coating. The second coating component concentration of profile B is a minimum at coating thickness T1 within the stent coating and increases to a maximum at the coating thickness TO at the exterior of the stent. Although the profiles A and B are shown as linear in this example, those skilled in the art will appreciate that the profiles can be simple or compound curves, and can include intermediate peaks or valleys above or below the concentrations illustrated at thicknesses zero, T1, T2, and TO. Likewise, the profiles A and B can overlap as shown or can be non-overlapping.

In one embodiment, the coated stent of FIG. 4C can be a binary drug coated stent. Profile A can be for a drug providing long-term therapy, such as an anti-proliferative drug. Profile B can be for a drug providing short-term therapy, such as an anti-inflammatory drug. Immediately after implantation, the coated stent delivers the anti-inflammatory drug to treat the tissue trauma from angioplasty and stent implantation. At a desired time, such as a few days to a few weeks, most of the anti-inflammatory drug will be gone and the coated stent delivers the anti-proliferative drug to prevent restenosis and tissue growth on the stent. The anti-proliferative drug delivery continues long term, such as a number of months or years. The continuously varying coating component concentration provides control over the timing and dosage of the two drugs. Multiple drug combinations, polymer combinations, and polymer/drug combinations can be used to achieve particular results.

Those skilled in the art will appreciate that coating component concentration versus coating thickness for a coated stent made in accordance with the present invention can be varied in a number of ways. The coating component concentration can be a compound curve with positive, negative and zero gradient, rather than simply increasing or decreasing. The coating component concentration can make step changes from changes of coating components or coating component concentration when applying the coating solution of solvent and coating component to the stent.

Figure 5:
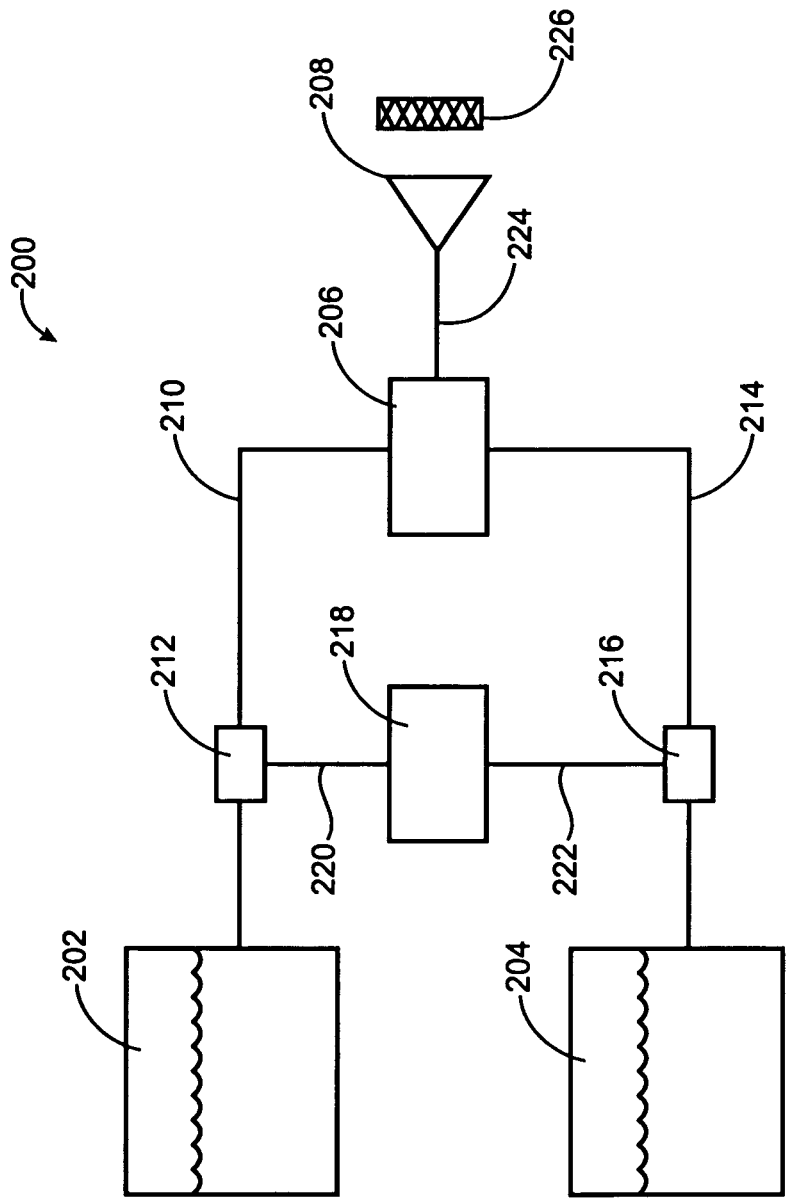
FIG. 5 shows a system for coating a stent in accordance with the present invention.

FIG. 5 shows a system for coating a stent in accordance with the present invention. At least two reservoirs containing coating solutions provide the coating solutions to a mixing volume, where they are mixed to form a gradient mixture. The gradient mixture is then provided to an applicator, which applies the gradient mixture to a stent. Such systems are used to provide gradient solutions to separation columns in high pressure or high performance liquid chromatography (HPLC). Examples of typical HPLC pumps and systems include the Rabbit-HP from Rainin Instrument, L.L.C.; Waters Alliance Systems from Waters Corporation; the 1100 Series from Agilent Technologies Inc.; the ProStar System from Varian, Inc.; and the LC 2010 system from Shimadzu Corporation.

The coating system 200 includes a first reservoir 202, a second reservoir 204, a mixing volume 206, and an applicator 208. Tube 210 connects the first reservoir 202 to the mixing volume 206 through first flow controller 212. Tube 214 connects the second reservoir 204 to the mixing volume 206 through second flow controller 216. Master controller 218 provides a first flow control signal 220 to the first flow controller 212 and a second flow control signal 222 to the second flow controller 216. Tube 224 connects the mixing volume 206 to the applicator 208, which applies the gradient mixture to a stent 226. The stent 226 can move relative to the applicator 208 by moving the stent 226, the applicator 208, or both, as desired.

In operation, the reservoirs 202, 204 are filled with coating solutions containing the desired concentrations of coating components. The master controller 218 adjusts the flow controllers 212, 216 as a function of time to regulate flow from the reservoirs 202, 204 to the mixing volume 206. The flow controllers 212, 216 set each flow from 0 to 100 percent, so flow from a single reservoir to the mixing volume is possible. The coating solutions from the reservoirs 202, 204 are mixed in the mixing volume 206 to form a gradient mixture, which is provided to the applicator 208 and applied to the stent 226.

The first reservoir 202 and second reservoir 204 can be any reservoirs suitable for containing first and second coating solutions to be applied to a stent. The coating solutions comprise one or more coating components dissolved or dispersed in a solvent, or solvent alone. The coating components include drugs, therapeutic agents, and polymers. Those skilled in the art will appreciate that almost a limitless number of continuous stent coatings can be achieved by selecting the coating solutions in the first reservoir 202 and second reservoir 204. In one embodiment, the first reservoir 202 contains a solvent/polymer/drug solution containing a first drug concentration and the second reservoir 204 contains a solvent/polymer/drug solution containing a second drug concentration. In another embodiment, the first reservoir 202 contains a solvent/polymer/drug solution containing a first drug and the second reservoir 204 contains a solvent/polymer/drug solution containing a second drug. In another embodiment, the first reservoir 202 contains a solvent/polymer/drug solution containing a first polymer and the second reservoir 204 contains a solvent/polymer/drug solution containing a second polymer. In yet another embodiment, the first reservoir 202 contains a solvent/drug solution and the second reservoir 204 contains a solvent/polymer solution, allowing a drug/polymer combination where the drug and polymer are incompatible or require incompatible solvents. Additional reservoirs can be used if more than two coating solutions are to be applied to the stent, with associated flow controllers and tubing to connect to the mixing volume.

The first flow controller 212 and second flow controller 216 can be any means for controlling flow from the reservoirs to the mixing volume, such as pumps, valves, and combinations thereof. In one embodiment, the flow controller is a metering pump. In another embodiment, the flow controller is a pump with a flow control valve. In another embodiment, the reservoir is pressurized and the flow controller is a flow control valve. In yet another embodiment, the flow controller is a syringe pump, which also acts as the reservoir.

The master controller 218 provides flow control signals 220, 222 to the flow controllers 212, 216 to control the flow of the first and second coating solutions from the reservoirs 202, 204 to the mixing volume 206. The master controller 218 can be a programmed general purpose computer, a microprocessor, or other control device. The relative flow rate of the first and second coating solutions determines the fraction of each coating solution applied to the stent. The master controller 218 can adjust the relative flow rate with time to provide a continuous gradient coating on the stent 226.

The mixing volume 206 can be any means for mixing flow from the first flow controller 212 and second flow controller 216 to form a gradient mixture. In one embodiment, the mixing volume 206 is a separate volume. In another embodiment, the mixing volume 206 is a portion of the tubing, such as a Y junction between the flow controllers and the applicator. In yet another embodiment as shown in FIG. 6, the mixing volume 206 is one of the reservoirs.

Referring to FIG. 5, the applicator 208 receives the gradient mixture from the mixing volume 206 and applies the gradient mixture to a stent 226. The concentrations of the coating components in the gradient mixture vary with time, so the application rate can be adjusted to provide the desired gradient profile in the stent coating. The applicator 208 can apply the gradient mixture by spraying, painting, wiping, rolling, printing, ink jet printing, or combinations thereof. Spraying can be ultrasonic or pressure spraying. Drying of the gradient mixture can be enhanced by nitrogen flow in the applicator 208. In one embodiment, a pump can be provided in the tube 224 after the mixing volume 206 and before the applicator 208 to provide pressure at the applicator 208.

Figure 6A:
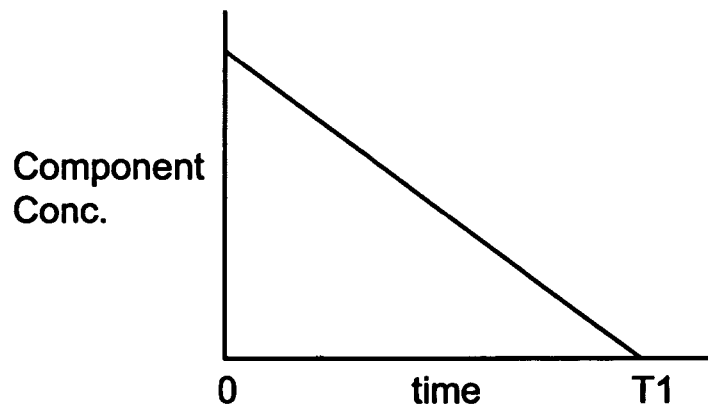
FIGS. 6A-6C show exemplary graphs of coating component concentration in the gradient mixture versus time for the coating system of FIG. 5.
Figure 6B:
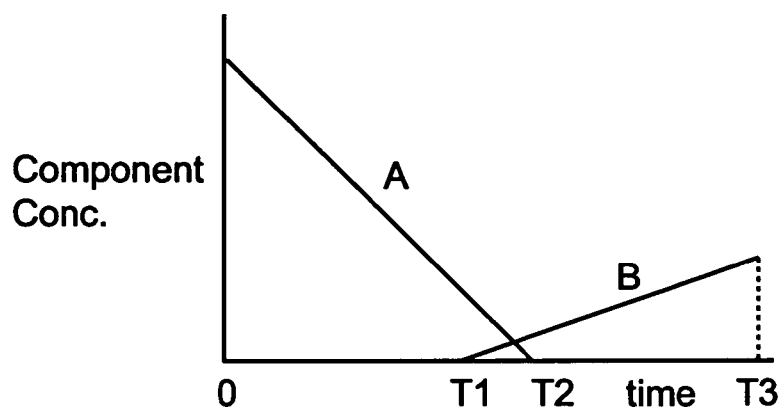
Figure 6C:
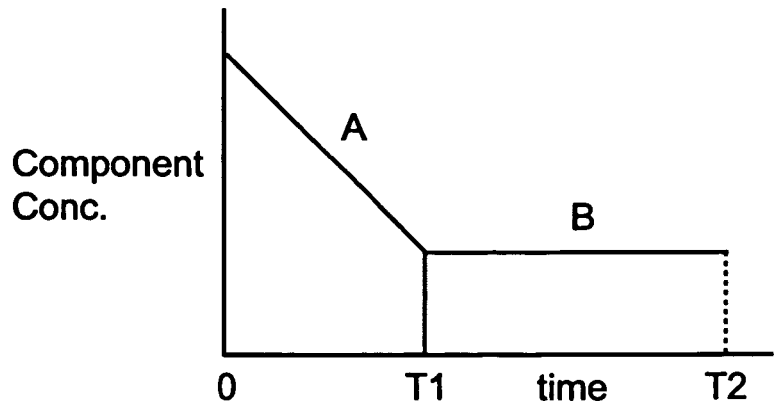

FIGS. 6A-6C show exemplary graphs of coating component concentration in the gradient mixture versus time for the coating system of FIG. 5. The coating component concentration in the gradient mixture being applied to the stent varies with time to vary the coating component concentration with coating thickness on the stent.

FIG. 6A shows an example of coating component concentration decreasing with time. In this example, the coating component concentration decreases linearly, although the decrease can follow a simple or compound curve. The higher concentration of the coating component is applied near the stent element and the lower concentration of the coating component is applied at the outer edge of the coating. When the coating component is a drug or other therapeutic agent, such a coating profile will suppress burst release and provide a steady long-term dose. In another embodiment, the coating component concentration could increase with time. Two reservoirs, each containing a coating solution, but with different coating component concentrations, can produce a decreasing or increasing coating component concentration. Each coating solution typically contains at least a solvent with a drug and/or polymer.

FIG. 6B shows an example of coating component concentration varying with time for a first and a second coating component. Profile A shows the coating component concentration for the first coating component decreasing from time 0 to time t2 and profile B shows the coating component concentration for the second coating component increasing from time t1 to time t3. In this example, the coating component concentrations change linearly, although the changes can follow an increasing or decreasing simple or compound curve. The higher concentration of the first coating component is applied near the stent element. The higher concentration of the second coating component is applied at the outer edge of the coating. In one embodiment, the first coating component is an anti-proliferative agent to provide long-term therapy and the second coating component is an anti-inflammatory agent to provide therapy immediately after stent implantation. Four reservoirs are required to produce this example: two reservoirs containing coating solutions with the first coating component, but different concentrations of the first coating component, and two reservoirs containing coating solutions with the second coating component, but different concentrations of the second coating component. Each coating solution typically contains at least a solvent with a drug and/or polymer.

FIG. 6C shows another example of coating component concentration varying with time for a first and a second coating component. Profile A shows the coating component concentration for the first coating component decreasing from time 0 to time t1, then going to zero. Profile B shows the coating component concentration for the second coating component going from zero to a constant value at time t1, then holding at the constant value from time t1 to time t2. The higher concentration of the first coating component is applied near the stent element. The concentration of the second coating component is constant throughout its thickness. In one embodiment, the first coating component is a drug or other therapeutic agent and the second coating component is polymer to provide a cap coat at the outer edge of the coating. Three reservoirs are required to produce this example: two reservoirs containing coating solutions with the first coating component, but different concentrations of the first coating component, and one reservoir containing a coating solution with the second coating component. Each coating solution typically contains at least a solvent with a drug and/or polymer.

Figure 7:
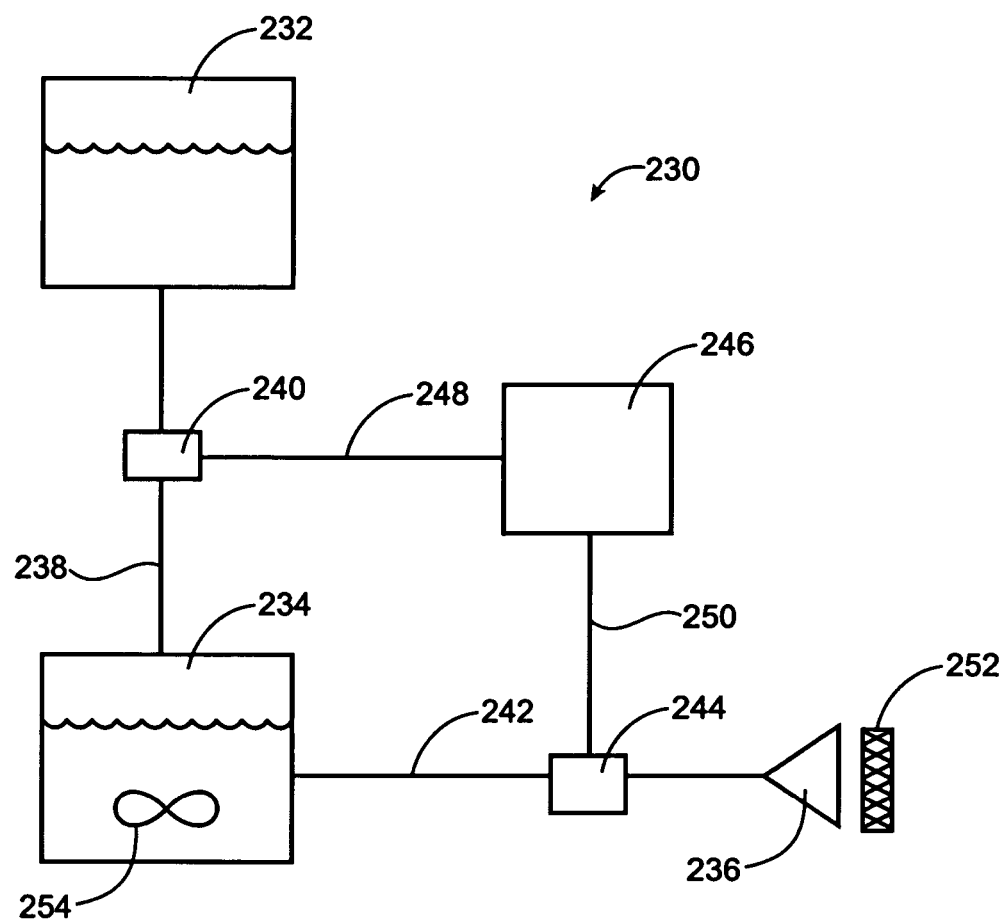
FIG. 7 shows another system for coating a stent in accordance with the present invention.

FIG. 7 shows another system for coating a stent in accordance with the present invention. At least two reservoirs contain coating solutions. One reservoir acts as both a reservoir and a mixing volume. The coating solution from one reservoir is transferred into the other reservoir, where they are mixed to form a gradient mixture. The gradient mixture is then provided to an applicator, which applies the gradient mixture to a stent. Such systems are used to provide pH and linear concentration gradients for chromatography and electrophoresis applications. One example of a typical system is the Gradient Mixer GM-1, Code Number 19-0495-01, available from Amersham Biosciences of Piscataway, N.J.

The coating system 230 includes a first reservoir 232, a second reservoir 234, and an applicator 236. Tube 238 connects the first reservoir 232 to the second reservoir 234 through first flow controller 240. Tube 242 connects the second reservoir 234 to the applicator 236 through second flow controller 244. Master controller 246 provides a first flow control signal 248 to the first flow controller 240 and a second flow control signal 250 to the second flow controller 244. The applicator 236 applies the gradient mixture to a stent 252. The stent 252 can move relative to the applicator 236 by moving the stent 246, the applicator 236, or both, as desired.

In operation, the reservoirs 232, 234 are filled with coating solutions containing the desired concentrations of coating components. The coating solution from the first reservoir 232 passes through the tube 238 and mixes with the coating solution in second reservoir 234 to form a gradient mixture. In this embodiment, the second reservoir 234 serves as both a reservoir and a mixing volume. An impeller 254 or other mixing device in the second reservoir 234 can be used to provide rapid, thorough mixing. The gradient mixture passes through the tube 242 to the applicator 236 and is applied to the stent 226.

The first flow controller 240 and second flow controller 244 can be any means for controlling flow from the first reservoir to the second reservoir and from the second reservoir to the applicator, such as pumps, valves, and combinations thereof. In one embodiment, the first flow controller 240 is omitted with gravity providing the driving force between the first reservoir 232 and the second reservoir 234. The second flow controller 244 is a peristaltic pump, which provides the gradient mixture to the applicator 236. The applicator 236 can be an ultrasonic spray head. In another embodiment, the flow controller is a metering pump. In another embodiment, the flow controller is a pump with a flow control valve. In yet another embodiment, the reservoir is pressurized and the flow controller is a flow control valve.

The applicator 236 can apply the gradient mixture by spraying, painting, wiping, rolling, printing, ink jet printing, or combinations thereof. Spraying can be ultrasonic or pressure spraying. Drying of the gradient mixture can be enhanced by nitrogen flow in the applicator 236.

The master controller 246 provides flow control signals 248, 250 to the flow controllers 240, 244 to control flow from the first reservoir 232 to the second reservoir 234 and from the second reservoir 234 to the applicator 236. The master controller 246 can be a programmed general purpose computer, a microprocessor, or other control device. In one embodiment, the master controller 246 adjusts the flow controllers 240, 244 as a function of time to regulate flow from the first reservoir 232 to the second reservoir 234 and/or from the second reservoir 234 to the applicator 236. In another embodiment, the master controller 246 is omitted and the flow controllers 240, 244 are set at a selected setting providing the desired flow rate, the same flow controller setting being used throughout the application process.

Figure 8:
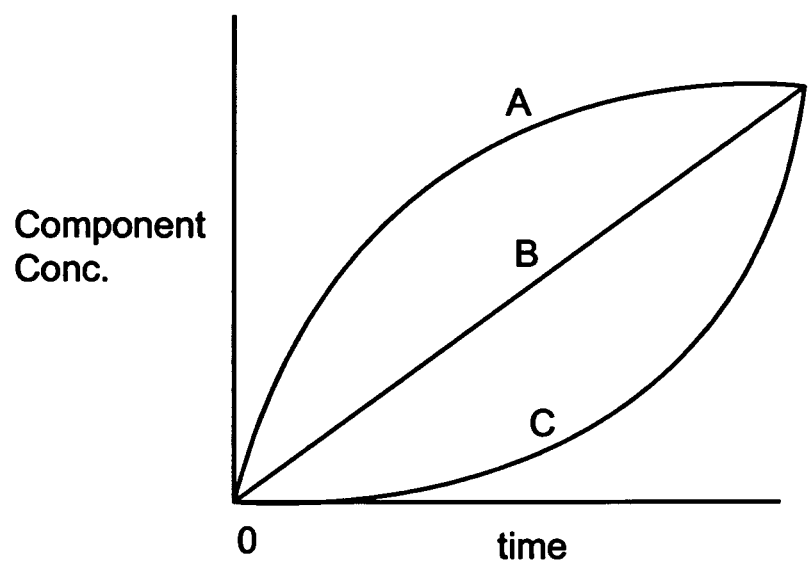
FIG. 8 shows exemplary graphs of coating component concentration in the gradient mixture versus time for the coating system of FIG. 7.

FIG. 8 shows exemplary graphs of coating component concentration in the gradient mixture versus time for the coating system of FIG. 7. The example of FIG. 8 assumes an initial concentration of a coating component in the first reservoir 232 and a lower concentration of the same coating component in the second reservoir 234. Profile B shows the case where the flow rate from the first reservoir 232 to the second reservoir 234 equals the flow rate from the second reservoir 234 to the applicator 208. The coating component concentration in the gradient mixture increases linearly from the concentration of coating component in the second reservoir 234 to the concentration of coating component in the first reservoir 232. Profile A shows the case where the flow rate from the first reservoir 232 to the second reservoir 234 is greater than the flow rate from the second reservoir 234 to the applicator 236, so that the coating component concentration in the gradient mixture increases more quickly than the linear case of Profile B. Profile C shows the case where the flow rate from the first reservoir 232 to the second reservoir 234 is less than the flow rate from the second reservoir 234 to the applicator 236, so that the coating component concentration in the gradient mixture increases more slowly than the linear case of Profile B. Those skilled in the art will appreciate that the cases presented in FIG. 8 are exemplary only and that many useful combinations are possible. For example, the reservoirs can contain coating solutions with different coating components and/or different coating component concentrations. The initial concentration of a coating component in the first reservoir 232 can be higher than concentration of the coating component in the second reservoir 234, so that the component concentration decreases with time, rather than increasing.

Figure 9:
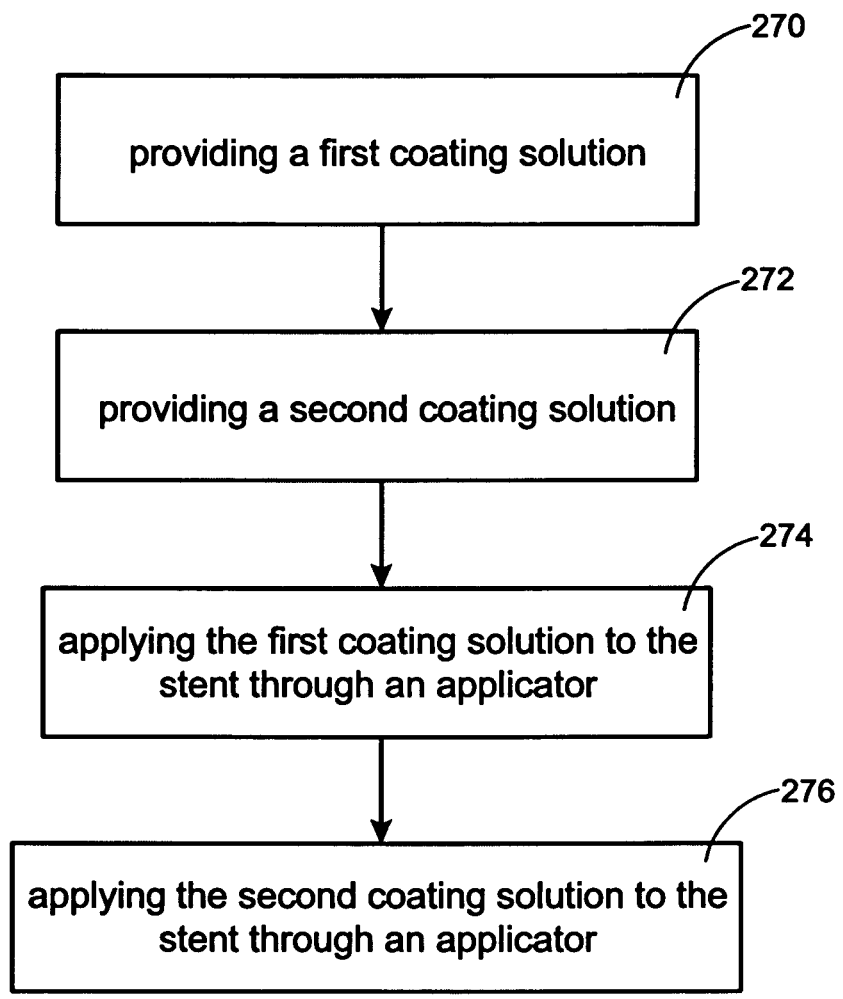
FIGS. 9 & 10 show methods of manufacturing a coated stent made in accordance with the present invention.

FIG. 9 shows a method of manufacturing a coated stent made in accordance with the present invention. A first coating solution is provided at 270 and a second coating solution is provided at 272. At 274, the first coating solution is applied to the stent through an applicator. At 276, the second coating solution is applied to the stent through the applicator.

In one embodiment, applying the first and second coating solutions to the stent through the applicator comprises mixing the first coating solution and the second coating solution to form a gradient mixture and applying the gradient mixture to the stent through the applicator. The first coating solution can include a first coating component and the concentration of the first coating component in the gradient mixture can be varied with time. The second coating solution can include a second coating component and the concentration of the second coating component in the gradient mixture can be varied with time. The coating components can be selected from drugs, therapeutic agents, polymers, bi-polymers, co-polymers, and combinations thereof. The mixing of the coating solutions shortly before application to the stent allows use of the method even if the first coating solution and the second coating solution are incompatible.

The variation of the concentration of one or both of the coating components with time can be selected as desired for a particular application. The concentration can vary linearly with time, increase with time, or decrease with time. The concentration of the first coating component can decrease with time, while the concentration of the second coating component increases with time. Those skilled in the art will appreciate that many combinations are possible to achieve a desired result.

Figure 10:
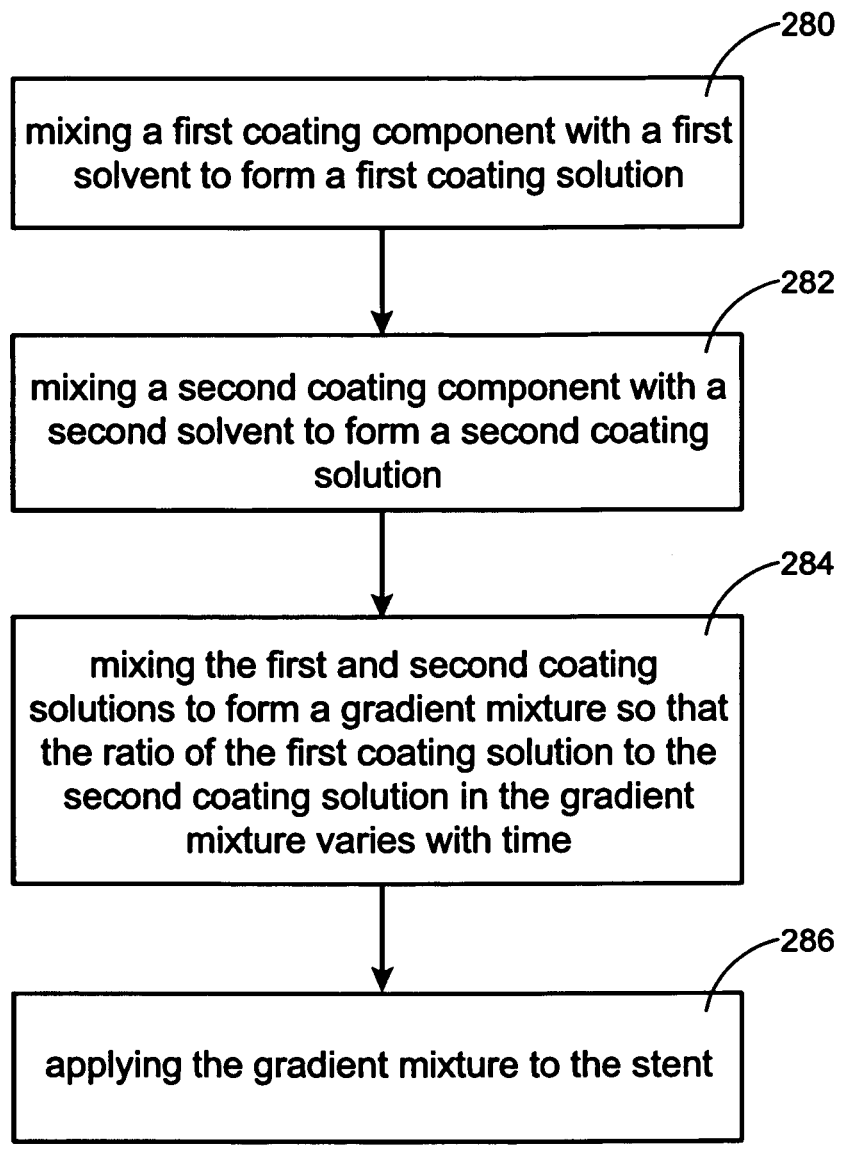

FIG. 10 shows another embodiment of a method of manufacturing a coated stent made in accordance with the present invention. A first coating component is mixed with a first solvent to form a first coating solution at 280 and a second coating component is mixed with a second solvent to form a second coating solution at 282. At 284, the first coating solution and the second coating solution are mixed to form a gradient mixture, so that the ratio of the first coating solution to the second coating solution in the gradient mixture varies with time. The gradient mixture is applied to the stent at 286.

In one embodiment, mixing the first and second coating solutions to form a gradient mixture comprises mixing the first coating solution and the second coating solution so that concentration of the first coating component in the gradient mixture varies with time. The coating components can be selected from drugs, therapeutic agents, polymers, bi-polymers, co-polymers, and combinations thereof. The mixing of the coating solutions shortly before application to the stent allows use of the method even if any pair of the first coating component, the first solvent, the second coating component, and the second solvent are incompatible with each other.

The variation of the concentration of one or both of the coating components with time can be selected as desired for a particular application. The concentration can vary linearly with time, increase with time, or decrease with time. The concentration of the first coating component can decrease with time, while the concentration of the second coating component increases with time. Those skilled in the art will appreciate that many combinations are possible to achieve a desired result.

It is important to note that FIGS. 1-10 illustrate specific applications and embodiments of the present invention, and is not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A stent delivery system comprising:
   a catheter;
   a balloon operably attached to the catheter;
   a stent disposed on the balloon; and
   a continuous coating disposed on the stent, the continuous coating having a thickness and comprising a first coating component and a second coating component, the first coating component being selected from the group consisting of drugs, therapeutic agents, polymers, co-polymers, bi-polymers, and combinations thereof;
   wherein, before implantation in a lumen, concentration of the first coating component varies continuously in a radial direction over at least part of the thickness of the continuous coating, and
   the concentration of the first coating component varies linearly over at least part of the thickness of the continuous coating.

2. The stent delivery system of claim 1 wherein concentration of the second coating component varies continuously over at least part of the thickness of the continuous coating.

3. The stent delivery system of claim 1 wherein:
   the continuous coating has an inner edge near the stent and an outer edge away from the stent; and
   concentration of the first coating component is highest at the inner edge and decreases in the direction of the outer edge.

4. The stent delivery system of claim 3 wherein the first coating component is an anti-proliferative agent.

5. The stent delivery system of claim 3 wherein concentration of the second coating component is highest at the outer edge and decreases in the direction of the inner edge.

6. The stent delivery system of claim 5 wherein the first coating component is an anti-proliferative agent and the second coating component is an anti-inflammatory agent.

7. The stent delivery system of claim 1 further comprising a cap coat disposed on the continuous coating.

8. A coated stent comprising:
   a stent, the stent having stent elements; and
   a continuous coating disposed on the stent elements, the continuous coating having a thickness and comprising a first coating component and a second coating component, the first coating component being selected from the group consisting of drugs, therapeutic agents, polymers, co-polymers, bi-polymers, and combinations thereof;
   wherein, before implantation in a lumen, concentration of the first coating component varies continuously in a radial direction over at least part of the thickness of the continuous coating, and
   the concentration of the first coating component varies linearly over at least part of the thickness of the continuous coating.

9. The coated stent of claim 8 wherein concentration of the second coating component varies continuously over at least part of the thickness of the continuous coating.

10. The coated stent of claim 8 wherein:
    the continuous coating has an inner edge near the stent and an outer edge away from the stent; and
    concentration of the first coating component is highest at the inner edge and decreases in the direction of the outer edge.

11. The coated stent of claim 10 wherein the first coating component is an anti-proliferative agent.

12. The coated stent of claim 10 wherein concentration of the second coating component is highest at the outer edge and decreases in the direction of the inner edge.

13. The coated stent of claim 12 wherein the first coating component is an anti-proliferative agent and the second coating component is an anti-inflammatory agent.

14. The coated stent of claim 8 further comprising a cap coat disposed on the continuous coating.

15. The stent delivery system of claim 1 wherein:
    the continuous coating has an inner edge near the stent and an outer edge away from the stent; and
    concentration of the first coating component is lowest at the inner edge and increases in the direction of the outer edge;
    wherein the first coating component is selected from the group consisting of drugs and therapeutic agents.

16. The stent delivery system of claim 1 wherein:
    the continuous coating has an inner edge near the stent and an outer edge away from the stent;
    concentration of the first coating component is lowest at the inner edge and increases in the direction of the outer edge; and
    concentration of the second coating component is highest at the inner edge and decreases in the direction of the outer edge;
    wherein the first coating component is an erodible polymer and the second coating component is a durable polymer.

17. The stent delivery system of claim 1 wherein the first coating component is a first drug and the second coating component is a second drug.

18. The stent delivery system of claim 1 wherein the first coating component and the second coating component are incompatible in solution.

19. The stent delivery system of claim 1 wherein the first coating component and the second coating component require incompatible solvents.

20. The coated stent of claim 8 wherein:
the continuous coating has an inner edge near the stent and an outer edge away from the stent; and
concentration of the first coating component is lowest at the inner edge and increases in the direction of the outer edge;
wherein the first coating component is selected from the group consisting of drugs and therapeutic agents.

21. The coated stent of claim 8 wherein:
the continuous coating has an inner edge near the stent and an outer edge away from the stent;
concentration of the first coating component is lowest at the inner edge and increases in the direction of the outer edge; and
concentration of the second coating component is highest at the inner edge and decreases in the direction of the outer edge;
wherein the first coating component is an erodible polymer and the second coating component is a durable polymer.

22. The coated stent of claim 8 wherein the first coating component is a first drug and the second coating component is a second drug.

23. The coated stent of claim 8 wherein the first coating component and the second coating component are incompatible in solution.

24. The coated stent of claim 8 wherein the first coating component and the second coating component require incompatible solvents.

25. A coated stent comprising:
a stent, the stent having stent elements; and
a continuous coating disposed on the stent elements, the continuous coating having a thickness and comprising a first coating component and a second coating component, the continuous coating having an inner edge near the stent and an outer edge away from the stent;
wherein, before implantation in a lumen, concentration of the first coating component varies continuously in a radial direction over at least part of the thickness of the continuous coating, and concentration of the second coating component varies continuously in the radial direction over at least part of the thickness of the continuous coating;
the concentration of the first coating component is highest at the inner edge and decreases in the direction of the outer edge;
the concentration of the second coating component is highest at the outer edge and decreases in the direction of the inner edge;
the first coating component is selected from the group consisting of polymers, co-polymers, bi-polymers, and combinations thereof; and
the second coating component is selected from the group consisting of drugs and therapeutic agents.

26. The coated stent of claim 25 wherein the second coating component is an anti-inflammatory agent.

27. The coated stent of claim 25 wherein the first coating component and the second coating component are incompatible in solution.

28. The coated stent of claim 25 wherein the first coating component and the second coating component require incompatible solvents.

29. A coated stent comprising:
a stent, the stent having stent elements; and
a continuous coating disposed on the stent elements, the continuous coating having a thickness and comprising a first coating component and a second coating component, the continuous coating having an inner edge near the stent and an outer edge away from the stent;
wherein, before implantation in a lumen, concentration of the first coating component varies continuously in a radial direction over at least part of the thickness of the continuous coating, and concentration of the second coating component varies continuously in the radial direction over at least part of the thickness of the continuous coating;
the concentration of the first coating component is highest at the inner edge and decreases in the direction of the outer edge;
the concentration of the second coating component is highest at the outer edge and decreases in the direction of the inner edge;
the first coating component is a first drug; and
the second coating component is a second drug different from the first drug.

30. The coated stent of claim 29 wherein the first coating component is an anti-proliferative agent and the second coating component is an anti-inflammatory agent.

31. The coated stent of claim 29 wherein the first coating component and the second coating component are incompatible in solution.

32. The coated stent of claim 29 wherein the first coating component and the second coating component require incompatible solvents.

33. A coated stent comprising:
a stent, the stent having stent elements; and
a continuous coating disposed on the stent elements, the continuous coating having a thickness and comprising a first coating component and a second coating component, the continuous coating having an inner edge near the stent and an outer edge away from the stent;
wherein, before implantation in a lumen, concentration of the first coating component varies continuously in a radial direction over at least part of the thickness of the continuous coating, and concentration of the second coating component varies continuously in the radial direction over at least part of the thickness of the continuous coating;
the concentration of the first coating component is lowest at the inner edge and increases in the direction of the outer edge;
the concentration of the second coating component is highest at the inner edge and decreases in the direction of the outer edge;
the first coating component is a first polymer; and
the second coating component is a second polymer different from the first polymer.

34. The coated stent of claim 33 wherein the first coating component is an erodible polymer and the second coating component is a durable polymer.

35. The coated stent of claim 33 wherein the first coating component and the second coating component are incompatible in solution.

36. The coated stent of claim 33 wherein the first coating component and the second coating component require incompatible solvents.

* * * * *